United States Patent
Inoue (10) Patent No.: US 7,221,735 B2
(45) Date of Patent: May 22, 2007

(54) RADIOGRAPHIC IMAGE CAPTURING APPARATUS, RADIOGRAPHIC IMAGE DISPLAY APPARATUS, AND METHODS THEREOF

(75) Inventor: Hitoshi Inoue, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 154 days.

(21) Appl. No.: 11/114,057

(22) Filed: Apr. 26, 2005

(65) Prior Publication Data

US 2005/0243967 A1 Nov. 3, 2005

(30) Foreign Application Priority Data

Apr. 30, 2004 (JP) .............................. 2004-136017

(51) Int. Cl.
*H05G 1/14* (2006.01)
(52) U.S. Cl. .......................... 378/97; 378/62; 378/108
(58) Field of Classification Search ................. 378/62, 378/96, 97, 108; 382/132
See application file for complete search history.

(56) References Cited

U.S. PATENT DOCUMENTS

2005/0244044 A1 11/2005 Inoue ......................... 382/132

OTHER PUBLICATIONS

Abstract of JH Siewerdsen et al., "DQE and System Optimization for Indirect-Detection Flat-Panel Imagers in Diagnostic Radiology", SPIE vol. 3336, pp. 546-555, Jul. 1998.

*Primary Examiner*—Courtney Thomas
(74) *Attorney, Agent, or Firm*—Fitzpatrick, Cella, Harper & Scinto (57) ABSTRACT

In a radiographic image capturing apparatus for capturing radiographic images by controlling a radiation generator and a detection device for converting an intensity distribution of radiation generated by the radiation generator into image information, the exposure conditions of each frame in dynamic image radiography are determined so as to set a total irradiation dose of radiation for the dynamic image radiography to be equal to or smaller than an irradiation dose required for a single static image radiography on the basis of the exposure condition of the dynamic image radiography. The dynamic image radiography is executed by capturing the radiographic image of each frame under the determined exposure conditions.

16 Claims, 10 Drawing Sheets

RADIOGRAPHIC IMAGE CAPTURING APPARATUS, RADIOGRAPHIC IMAGE DISPLAY APPARATUS, AND METHODS THEREOF

FIELD OF THE INVENTION

The present invention relates to a technique for imaging a radiation intensity distribution and, more particularly, to a technique suited to capture medical X-ray images.

BACKGROUND OF THE INVENTION

As the most popular method of noninvasively observing the interior of a human body and using the observation result in medical diagnosis, direct imaging of the transmittance distribution of X-rays transmitted through the human body is known. As such imaging method, a conventional method of imaging a fluorescence distribution due to X-rays that reach a phosphor using a silver halide film, a method of amplifying photoelectrons due to fluorescence using an image intensifier, and visualizing them using a TV camera, and a method of exciting latent image information formed by an X-ray intensity distribution on a photostimulable phosphor using a laser beam, and reading and visualizing the information are known. Furthermore, in recent years, a method of imaging the spatial distribution of free electrons generated in a heavy metal by fluorescence or X-ray radiation using a flat panel detector (FPD) which comprises a large-scale solid-state image sensing element that can cover the entire chest of a human body is put into practical applications due to the development of semiconductor technology.

The motions of a human body can be separated into parts such as a heart, gastro-intestinal, and the like that move depending on only the autonomic nerve, and parts such as respiration, four limbs, and the like that can also be moved intentionally. In conventional static image radiography, X-ray images are radiographed as static images since the part that can be moved intentionally can also be kept static intentionally. This is because a radiographic apparatus mainly uses a silver halide film or photostimulable phosphor. However, it is important to observe dynamic states of even such parts in the medical sense of the term. When such part is intentionally moved upon radiography without being kept static intentionally, since the rate of motion can be controlled, an exposure rate in tune with motion need not be set unlike that for the heart. For example, upon observing the respiratory behavior of a lung field, if a patient respires relatively slowly, the dynamic state can be satisfactorily observed even at an exposure rate of, e.g., about 3 frames per sec. However, it is difficult for a patient to intentionally move a given part too slowly, and respective parts have appropriate motion rates.

Conventionally, upon observing the dynamic states depending on the autonomic nerve, since such parts are limited ones, i.e., a heart, artery, gastro-intestinal, and the like, a required part can be radiographed using a TV camera system using an image intensifier. In this case, the exposure rate is important.

On the contrary, an imaging area is important in place of the exposure rate upon radiographing a part that can be moved intentionally, especially, upon radiographing the respiratory behavior of a lung field. For example, in order to observe a lung function from a dynamic state, various aspects from the motion of a diaphragm to that of veins inside the lung field must be observed. Therefore, the image intensifier with a limited imaging area cannot be used, and dynamic state observation must be done at a rate of about three frames per sec by exchanging large-sized films at high speed. However, in order to realize such radiography, a mechanism for exchanging large-sized films at high speed is required, and X-ray irradiation of a considerable dose is required to image films. For this reason, in order to obtain a plurality of images for dynamic state observation, huge dose and cost are required, and such method is far from practical use. Also, no method for optimally observing such plurality of images is available.

In recent years, along with the development of a large-sized X-ray FPD, the dynamic state of a human body over a relatively broad range (e.g., a chest) can be captured without any mechanical operations (e.g., those for exchanging films at high speed). However, even FPDs of practical use in terms of cost are those which have sensitivity equivalent to conventional films. Hence, the FPD does not have sensitivity as high as the TV system using the image intensifier, and requires a considerable dose to capture an image with sufficiently high image quality. For example, "J. H. Siewerdsen, L. E. Antonuk; DQE and System Optimization for Indirect-Detection Flat-Panel Imagers in Diagnostic Radiology; SPIE Vol. 3336", a dose of X-rays that normally reach a sensor in chest static image radiography is 3 mR (milli-roentgens), and if a plurality of images for dynamic state observation are radiographed at this dose, a considerable dose is required.

SUMMARY OF THE INVENTION

The present invention has been in consideration of the above problems, and has as its object to prevent an increase in dose in dynamic image radiography.

According to one aspect of the present invention, there is provided a radiographic image capturing apparatus for capturing radiographic images by controlling a radiation generator and a detection device for converting an intensity distribution of radiation generated by the radiation generator into image information, comprising: a determination unit configured to determine an exposure condition of each frame in dynamic image radiography so as to set a total irradiation dose of radiation for the dynamic image radiography to be equal to or less than an irradiation dose required for a single static image radiography on the basis of the exposure condition of the dynamic image radiography; and a capturing unit configured to capture a radiographic image of each frame under the exposure condition determined by the determination unit.

According to another aspect of the present invention, there is provided a radiographic image display apparatus which sequentially and selectively displays a plurality of radiographic images captured by dynamic image radiography which has a total exposure dose equal to or less than static image radiography, comprising: a detection unit configured to detect a pixel value of a non-imaging area caused by an insufficient radiation dose on the basis of a frequency distribution of pixel values obtained for one of the plurality of radiographic images; a gray-level transformation unit configured to perform gray-level transformation to ignore pixel values of the non-imaging area detected by the detection unit; and a display unit configured to display image data that has undergone the gray-level transformation by the gray-level transformation unit on a display.

Other features and advantages of the present invention will be apparent from the following description taken in conjunction with the accompanying drawings, in which like

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will now be described in detail in accordance with the accompanying drawings.

First Embodiment

The present inventor found that not only a dose per frame of image information but also a total dose upon dynamic image radiography are important in X-ray dynamic image observation. This is because an "improvement effect of image quality to be recognized" due to an afterimage effect of the human eye and recognition, and unintentional and intentional tracing of a moving object is present. For example, image capturing is attempted to a still subject using two methods. In one method, a static image radiographed at a given specific X-ray dose is observed. In the other method, a plurality of images are radiographed to obtain the above specific X-ray dose as a total, and are observed as a dynamic image. In a theoretical sense, since all the plurality of images of the latter method are added and averaged, the average image is quite the same as the image of the former method in a sense of quantum mottle, and has the same image quality as that of the static image of the former method. When the images of the latter method are repetitively observed as a dynamic image, substantially the same effect as averaging of arithmetic operations is produced due to the afterimage effect of the human eye and recognition although it depends on the display rate of the dynamic image, thus allowing the same recognition as in a static image.

When a subject moves, and its dynamic image is observed, a person unintentionally recognizes the structure of an object, and inevitably traces and observes its movement. As a result, as for one part, the same averaging effect as in the above description occurs, and recognition equivalent to a static image is allowed.

The averaging obtained by the afterimage effect of the human eye and recognition is not established unless a total dose of the plurality of images is sufficient, but if the dose is equivalent to the static image, the images are observable. Therefore, when dynamic state X-ray images are captured and observed using the same image receiving apparatus as a static image, the total dose upon dynamic image radiography can be set to be equal to that of a static image so as to obtain the same information volume as the static image. Depending on required image information for dynamic state observation, the total dose upon dynamic image radiography can be decreased.

In the embodiments to be described below, upon dynamic image radiography is made to "suppress the total exposure dose upon dynamic image radiography to be equal to or lower than that upon static image radiography".

For this reason, in the first embodiment, static image radiography and dynamic image radiography are successively done using one FPD, and the total dose of the dynamic image radiography is set to be equal to that in static image radiography performed immediately before the dynamic image radiography. That is, since a static image is radiographed prior to the dynamic image radiography, an X-ray dose required for static image radiography is monitored, and the monitoring result is used to set a dose of the dynamic image radiography. In this case, a dose twice that of the static image radiography alone is required. However, in general static image radiography, re-radiography of an image called "radiation error" due to a radiographic failure is often performed. In such case as well, a dose twice that of the static image radiography alone is required. Hence, the dose of such level does not have any adverse effect on the human body.

Figure 1:
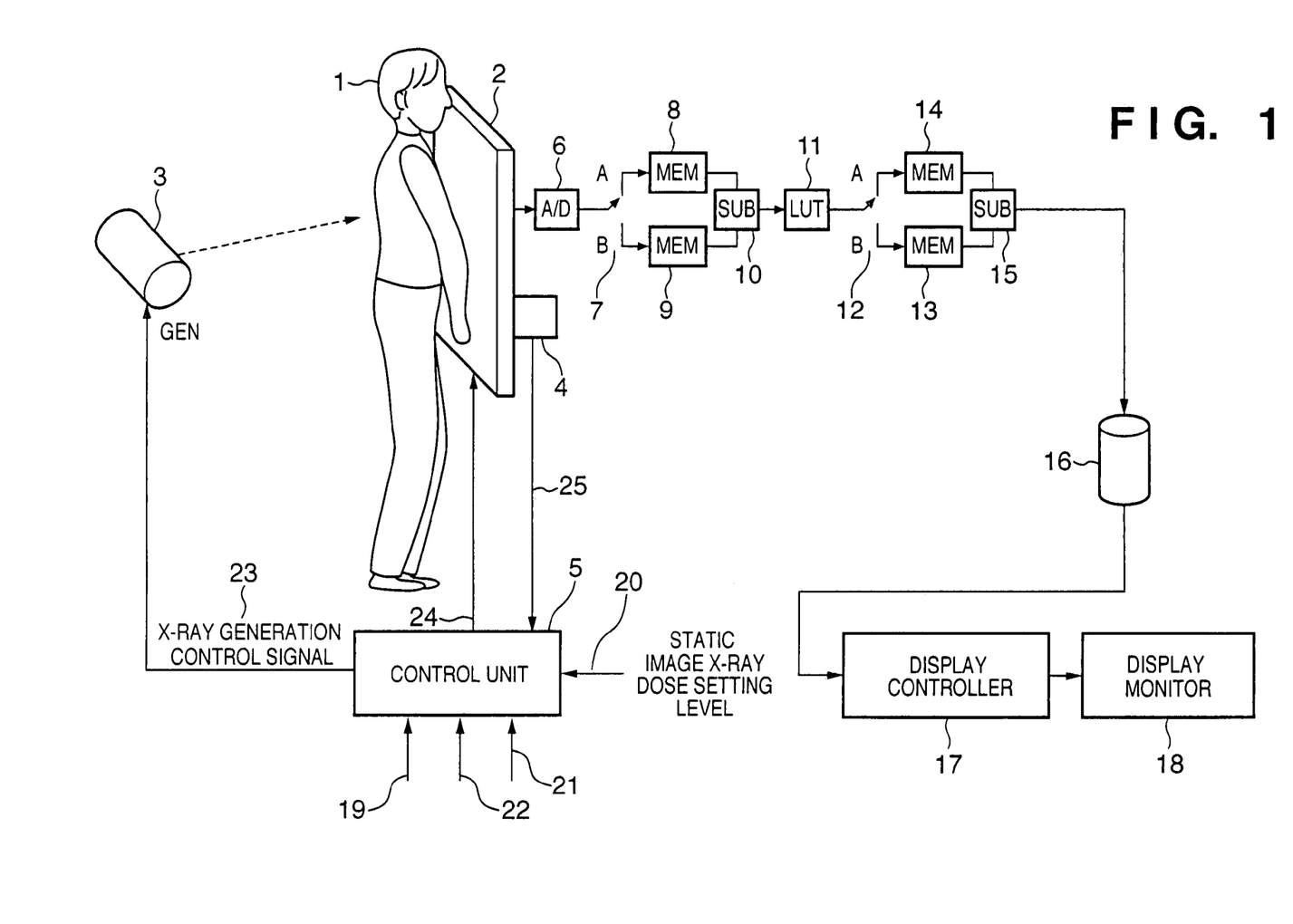
FIG. 1 is a block diagram showing the arrangement of a radiographic image capturing apparatus according to the first embodiment.

FIG. 1 is a block diagram showing an example of the arrangement of an X-ray image capturing apparatus and display apparatus according to the first embodiment. Referring to FIG. 1, X-rays generated by an X-ray generator 3 are transmitted through a subject 1, and reach an X-ray flat panel detector (FPD) 2. The FPD 2 images the dose distribution of the X-rays. Note that the FPD 2 holds an anti-scattering grid (not shown) for removing scattering X-rays from the subject 1 and the like. The FPD 2 has a spatial sampling pitch of at least 1 mm or less so as to image the human body to a nicety. Note that a tube voltage and tube current value as X-ray generation conditions of the X-ray generator 3 can be set from a control unit 5, and can be adjusted in accordance with a subject and exposure purpose.

A phototimer 4 as an X-ray dose monitor is provided to set an appropriate X-ray dose upon static image radiography. The phototimer 4 outputs an X-ray dose that has passed a specific part of the subject 1 onto a signal line 25. This signal is accumulated by the control unit 5. When the accumulated value reaches a given value, X-rays are cut off under the control of the control unit 5, since the X-ray dose large enough to radiograph a static image is obtained.

The control unit 5 controls the X-ray generator 3 and FPD 2. As described above, the control unit 5 accumulates a signal from the phototimer 4, and controls to cut off X-rays generated by the X-ray generator 3 on the basis of the accumulated value, and to continuously output X-ray pulses with a required pulse width from the X-ray generator 3. The control unit 5 has an arrangement for inputting and setting an irradiation start trigger 19 used to start X-ray irradiation, a static image X-ray dose setting level 20 (an X-ray dose level required to radiograph a static image) to be compared with the accumulated value of the phototimer output, a frame count 21 upon capturing an image (to be also referred to as a dynamic image hereinafter) for dynamic state observation, and a dynamic image radiography time 22. The control unit 5 outputs a control signal 23 to the X-ray generator 3, a control signal 24 of the FPD 2, and the like.

An A/D converter 6 converts the output from the FPD 2 into a digital value. A switch 7 switches data storage destinations for a dark output and image output of the FPD 2. The dark output is an output captured from the FPD 2 when no X-rays are irradiated, and is saved in an image memory 9 by connecting the switch 7 to the B side. On the other hand, the image output is an output captured from the FPD 2 when X-rays are output, and is saved in an image memory 8 by connecting the switch 7 to the A side. Note that the dark output can be captured at any timing before and after the image output. A subtractor 10 subtracts the dark output stored in the image memory 9 from the image output stored in the image memory 8. With this process, offset correction for the image output is made.

A lookup table unit 11 has an LUT (Look-Up Table), and converts image data offset-corrected by the subtractor 10 into a log value. Since the image data is converted into a log value, a subtraction process later performs an operation of division. A switch 12 is used to switch a gain image and subject image of the FPD 2. The gain image is obtained by capturing the output from the FPD 2 upon radiation of X-rays without any subject, subtracting the dark output from that output, and converting the difference into a log value by the LUT unit 11. The gain image is recorded on a gain image memory 13 by connecting the switch 12 to the B side. The offset-corrected subject image is recorded on a memory 14 by connecting the switch 12 to the A side. A subtractor 15 subtracts the data stored in the gain memory 13 from the offset-corrected image data stored in the memory 14. With the subtraction process by the subtractor 15, gain variations for respective pixels on the FPD 2 can be corrected. If the FPD 2 has a defective pixel which is not imaged (not shown in FIG. 1), an arrangement for repairing (interpolating) such defective pixel using surrounding normal pixel values is provided. The image data obtained in this way is saved in a data recording device 16. The image data saved in the data recording device 16 is read out by a display controller 17, and is displayed on a display monitor 18.

The arrangement of the control unit 5, and an X-ray imaging process will be described in more detail below.

Figure 2:
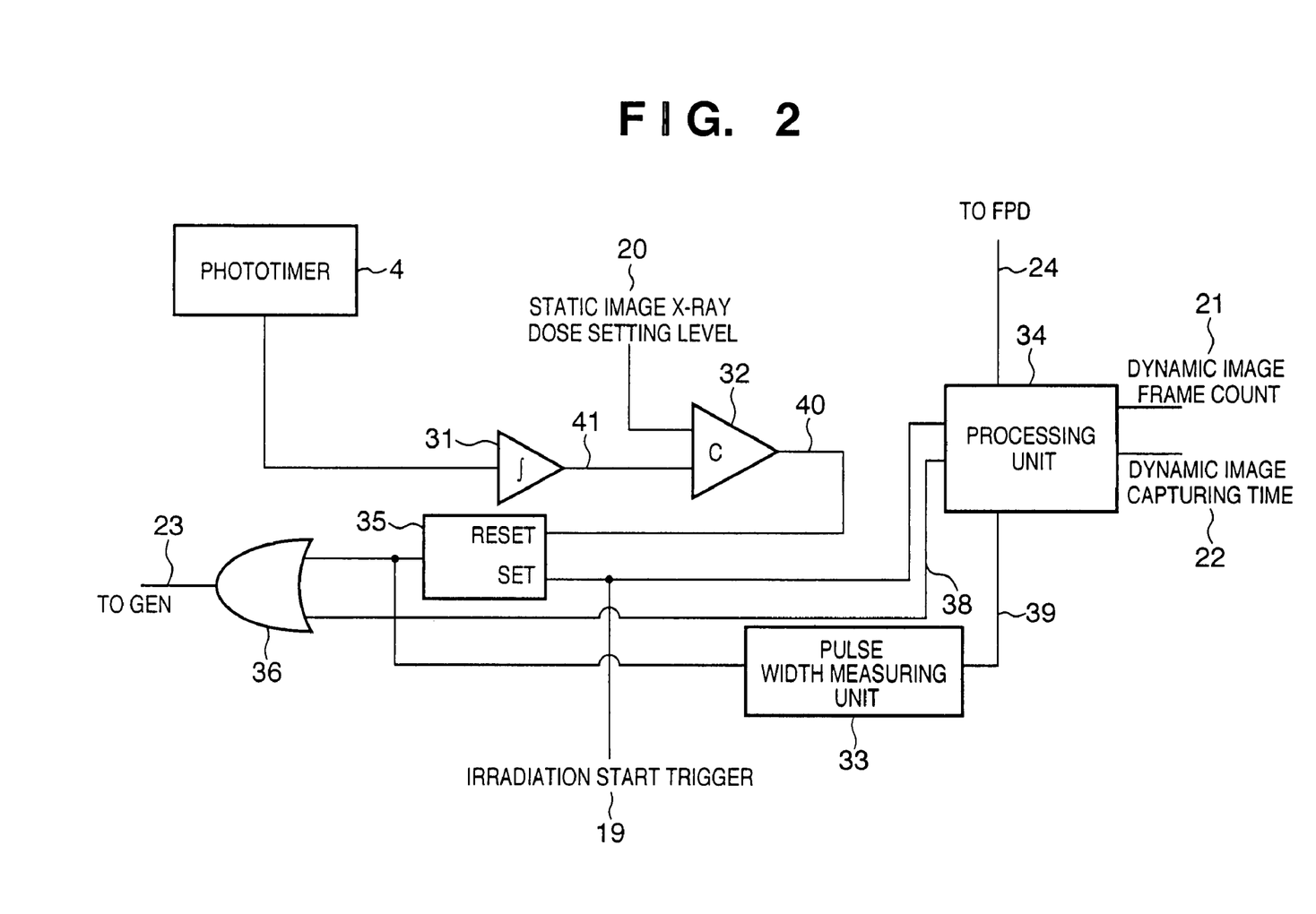
FIG. 2 is a block diagram showing the arrangement of a control unit.

FIG. 2 is a block diagram showing the detailed arrangement of the control unit 5. Referring to FIG. 2, an integrator 31 integrates a signal from the phototimer 4, i.e., a signal indicating the X-ray dose that has passed a specific part of the subject 1. An integrated output 41 is input to a comparator 32. The comparator 32 compares the set static image X-ray dose setting level 20 with the integrated output 41, and outputs a comparison result 40.

A flip-flop 35 is set by the irradiation start trigger 19, and is reset by the comparison result 40 output from the comparator 32. A signal output from the flip-flop 35 is used as the X-ray generation control signal 23. A processor unit 34 incorporates a microprocessor, and receives the externally set dynamic image frame count 21 and dynamic image radiography time 22. The processing unit 34 also receives the irradiation start trigger 19 to detect the irradiation start timing, and outputs an X-ray control pulse 38 for a dynamic image. The processing unit 34 controls the image exposure timing of the FPD 2 via a signal line 24 so as to capture image data in synchronism with the X-ray control pulse 38. The processing unit 34 acquires the pulse width of X-ray irradiation upon static image radiography from a pulse width measuring unit 33 via a signal line 39. The pulse width measuring unit 33 measures an X-ray pulse width (the pulse width of the output from the flip-flop 35) upon static image radiography, and supplies the measurement result to the processing unit 34. An OR gate 36 supplies the X-ray control pulse for static image radiography from the flip-flop 35 or the X-ray control pulse for dynamic image radiography from the processing unit 34 to the X-ray generator 3. That is, the output from the OR gate 36 is supplied to the X-ray generator 3 in FIG. 1 as the X-ray control signal 23.

Figure 3:
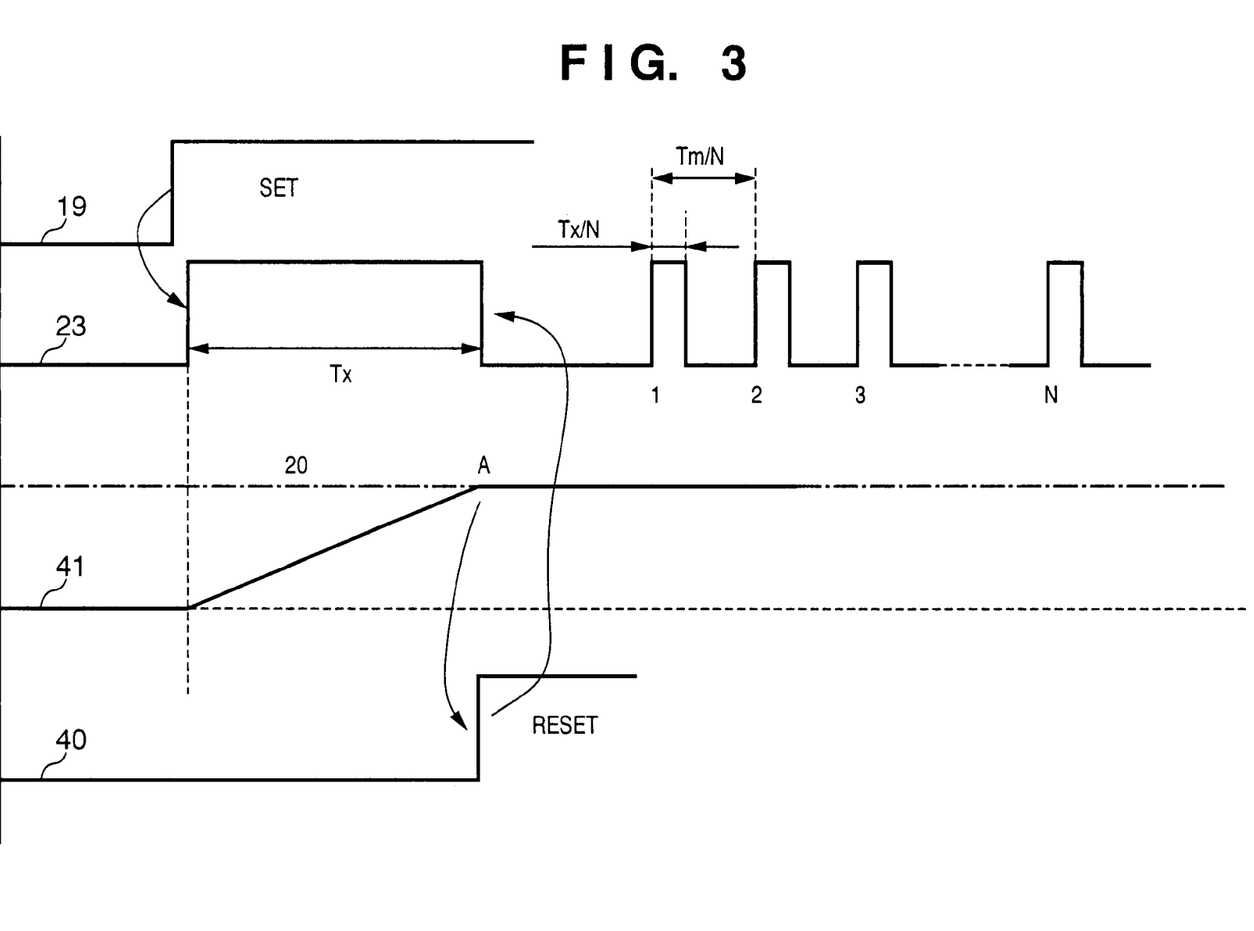
FIG. 3 is a timing chart of static image radiography and dynamic image radiograph according to the first embodiment.

The X-ray imaging operation of the control unit 5 will be described below using the timing chart of FIG. 3. Let N be the dynamic image frame count and Tm be the dynamic image radiography time, which are set in dynamic image radiography. As shown in FIG. 3, the flip-flop 35 is set in response to the leading edge of the irradiation trigger 19, thus generating the X-ray generation control signal 23. While the X-ray generation control signal 23 is ON, X-rays are emitted, and static image radiography is done. When the X-rays are emitted, the phototimer 4 outputs a signal indicating the X-ray dose that reaches the phototimer 4, and the integrated output 41 from the integrator 31 increases, as shown in FIG. 3. The integrated output 41 is compared with the static image X-ray dose setting level 20 by the comparator 32, and a target dose (static image X-ray dose setting level 20) is reached at a timing A in FIG. 3. The comparator 32 outputs the comparison result 40 at the timing A. That is, since the comparison result 40 goes to high level, the flip-flop 35 is reset, the X-ray generation control signal 23 is set OFF, and X-ray irradiation is stopped. As a result, the X-ray generation control signal 23 is output as an X-ray control pulse with a width Tx, as indicated by the second column in FIG. 3, and X-rays are output from the X-ray generator 3 during the period of this pulse.

The pulse width measuring unit 33 measures the pulse width (time) Tx of the X-ray generation control signal 23. Since the dynamic image radiography time Tm and the frame count N are set, as described above, the processing unit 34 calculates a pulse width (Tx/N) for dynamic image radiography, and a time (Tm/N) to be assigned per frame of a dynamic image upon reception of Tx from the pulse width measuring unit 33. The processing unit 34 outputs a pulse with the width Tx/N as the X-ray generation control signal to have Tm/N as a pulse period. As a result, N dynamic image pulses are output, as indicated by the latter half in the second column of FIG. 3. In this way, dynamic image radiography is executed immediately after static image radiography, and the total X-ray dose for this dynamic image radiography has the same level as the static image.

Upon determining the dynamic image pulses, the total X-ray dose need not always be the same as that of the static image, but a relatively smaller X-ray dose may be set in accordance with the purpose and the load on a patient. Details of this setting will be described later.

When the aforementioned operation is applied upon radiographing a respiratory behavior in practice, a patient takes in breath in an initial stage, holds his or her breath in a maximum inhalation state, and undergoes static image radiography in accordance with operator's instructions. Upon completion of the static image radiography, the patient begins to respire slowly, and the respiration state is successively captured as a dynamic state.

The processing unit 34 in FIG. 2 executes the aforementioned imaging process when the microprocessor executes a program. That process will be described in more detail below with reference to the flowcharts shown in FIGS. 4 and 5.

Figure 4:
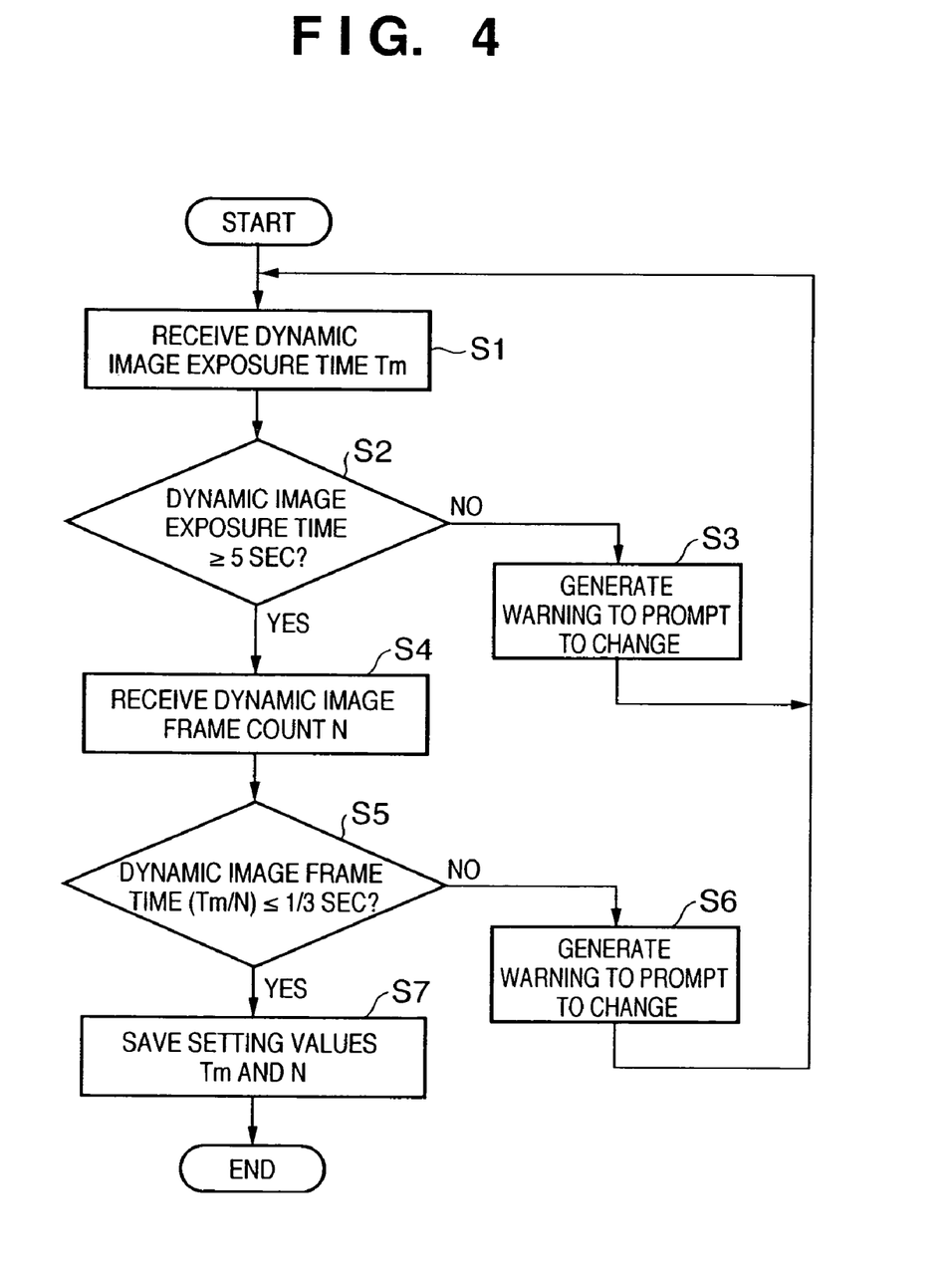
FIG. 4 is a flowchart showing the process upon reception of parameters by a processing unit.

FIG. 4 shows the process for receiving the dynamic image frame count and dynamic image radiography time. Although not shown in FIGS. 1 and 2, the operator inputs a required dynamic image radiography time Tm and dynamic image frame count N using an appropriate user interface. In the process shown in the flowchart of FIG. 4, it is checked if the input values are appropriate, and if they are appropriate, setting values are saved.

After the image exposure time Tm is received in step S1, it is checked in step S2 if that time is 5 sec or more. If the time of less than 5 sec is designated, the flow advances to step S3, and a warning is generated to prompt the operator to change the image exposure time. If the time of 5 sec or more is set, the flow advances to step S4, and the designated dynamic image count N is received. Note that the reason why the dynamic image radiography time Tm is set to be 5 sec or more will be described later. Using the designated frame count N and dynamic image radiography time Tm, a moving frame time Tm/N corresponding to a frame period of a dynamic image is calculated, and it is checked if this value is ⅓ sec. If this value is not ⅓ sec or less, the flow advances to step S6, and a warning is generated to prompt the operator to change the setting of the frame count. If the calculated value is ⅓ sec or less in step S5, the flow advances to step S7, and the setting values Tm and N are held in a memory (not shown) in the processing unit 34. Note that the reason why the moving frame time is set to be ⅓ sec or less will be described later.

Note that parameters to be determined in this setting include three parameters, i.e., "dynamic image radiography time (Tm)", "dynamic image frame count (N)", and "dynamic image frame time (Tm/N)". These three parameters are associated with each other, and if two parameters are determined, the remaining one parameter can be calculated automatically. Hence, in FIG. 4, "dynamic image radiography time Tm" and "dynamic image frame count N" are input. However, other combinations of two parameters may be input. In this case as well, the conditions, i.e., the dynamic image radiography time of 5 sec or more, and the dynamic image frame time Tm/N of ⅓ sec or less are checked to meet conditions that allow appropriate dynamic image observation.

In this embodiment, the dynamic image radiography time is set to be 5 sec or more, and the exposure rate of dynamic images is three frames or more per sec. The reason for this is as follows. As has been described in the paragraphs of the prior art, when a human body is intentionally moved by, e.g., respiration or the like, its moving rate has a lower limit. For example, even when respiration is intentionally slowed down, a rate of 5 sec per inhalation, and that of 5 sec per exhalation are limits (one motion is complete for 5 sec independently of parts). If a rate lower than the limit is set, a motion becomes very awkward, and a stable motion cannot be expected. The present inventor found that stable trace recognition cannot be made until images are captured at 3 frames or more per sec upon imaging and observing such motion. The dynamic image radiography time of 5 sec or more is required since one motion is done for 5 sec. Upon observing the respiratory behavior of a chest, it is important to use an FPD having a size that can cover the entire chest of the human body. Note that it is desirable to set an upper limit in the dynamic image radiography time. In case of this embodiment, since the inhalation/exhalation rate of 5 sec is a lower limit that can assure a stable motion, an upper limit of 10 sec or less may be set.

Figure 5:
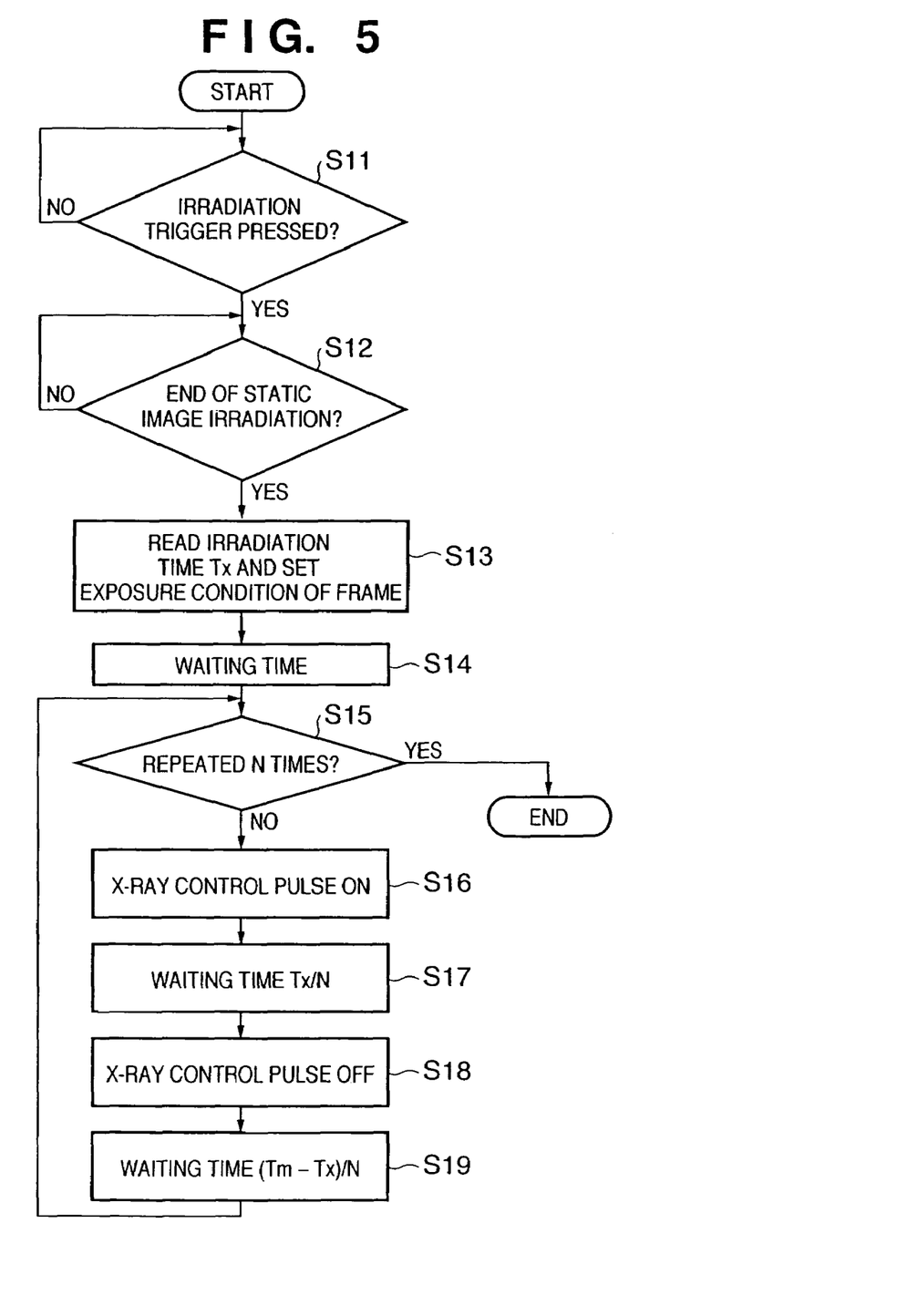
FIG. 5 is a flowchart showing the process upon static image radiography and dynamic image radiograph by the processing unit.

FIG. 5 is a flowchart for explaining the control of the processing unit 34 when radiography is actually made after dynamic image parameters are determined. The operation described with reference to the timing chart in FIG. 3 is implemented when the processing unit 34 executes the process in FIG. 5.

In steps S11 and S12, the X-ray irradiation start and end timings in static image radiography are determined. In this embodiment, the X-ray irradiation start timing is determined by monitoring the irradiation trigger input 19, and the X-ray irradiation end timing is determined by monitoring the output from the pulse width measuring unit 33. Note that the X-ray irradiation start and end timings may be determined by monitoring the output signal from the flip-flop 35. In step S13, the irradiation time Tx required for the static image radiography is read out, and exposure conditions of respective frames are set using the set frame count N and dynamic image radiography time Tm. For example, the irradiation time per frame is set to be Tx/N, and the frame cycle (irradiation cycle) is set to be Tm/N. Image data captured at that time is stored in the data recording device 16 via the respective units shown in FIG. 1. In step S14, a waiting time is set until the beginning of dynamic image radiography. The waiting time is appropriately set according to the motion of a patient, and may be omitted. Alternatively, the flow may advance to step S15 and subsequent steps in response to an operation input that instructs to start dynamic image radiography.

After the dynamic image radiography starts, processes in steps S15 to S19 are executed. It is checked in step S15 if dynamic image pulses have been output N times. For example, a counter memory is accumulated every time X-ray irradiation per frame is made, thus checking if N irradiations (end of radiography for N frames) have been made. If N irradiations have not been made yet, the dynamic image X-ray control pulse 38 is output to irradiate X-rays in accordance with the timing shown in FIG. 3. That is, the dynamic image X-ray control pulse 38 is set ON in step S16, the control waits for a waiting time Tx/N in step S17, and X-ray control pulse 38 is set OFF in step S18 when the waiting time Tx/N has passed. In this manner, irradiation for one frame is completed. The control then waits for a waiting time (Tm−Tx)/N for a pulse interval in step S19, and the flow returns to step S15. The aforementioned processes are repeated N times (step S15), thus obtaining N X-ray images (frame images). In this case as well, frame images are sequentially stored in the data recording device 16 via respective processing units in FIG. 1 every time the X-ray pulse is generated.

Note that an appropriate numerical value $\alpha$ ($\alpha \geq 0$) is used by setting the waiting time in step S17 as (Tx−α)/N and setting the waiting time in step S19 as (Tm−Tx+α)/N, so that the dynamic image radiography dose can be reduced in accordance with the purpose intended and the load on the patient. When α is set to be less than 0, the total irradiation dose upon dynamic image radiography is set to be larger than that upon static image radiography. In this embodiment, $\alpha \geq 0$ is set so as to set the total irradiation dose upon dynamic image radiography to be equal to or smaller than that upon static image radiography. Also, the irradiation dose upon dynamic image radiography may be set to exceed that upon static image radiography within a predetermined allowable range. For example, when the frame count N is large, an X-ray dose per frame becomes small. Hence, if N is larger than a predetermined value, α may be set to be a negative value in accordance with N.

The FPD 2 may change the output voltage gain by changing the internal amplifier gain or the capacity for holding image information in accordance with an external input setting. In this case, the output voltage gain upon static image radiography may be changed from that upon dynamic image radiography.

As described above, according to the first embodiment, since the total irradiation dose upon dynamic image radiography is controlled to be equal to that upon capturing a static image using the same apparatus, dynamic image data that allow dynamic state observation can be captured with a safe dose.

Second Embodiment

In the first embodiment, the X-ray dose upon static image radiography is monitored. However, the irradiation dose required to capture a static image is empirically known without any measurement. For example, according to the aforementioned reference (J. H. Siewerdsen, L. E. Antonuk; DQE and System Optimization for Indirect-Detection Flat-Panel Imagers in Diagnostic Radiology; SPIE Vol. 3336), a dose of X-rays that normally reach a sensor in chest static image radiography is 3 mR or less. Hence, in the second embodiment, a maximum total dose of X-rays that reach a sensor upon dynamic image radiography is set to be 3 mR or less. That is the total X-ray dose is set to be 3 mR as a dose upon normal static image radiography, and chest dynamic image radiography is conducted without any static image radiography.

More specifically, an X-ray dose Ax of a specific ray quality (tube voltage) is measured for a predetermined time T0 using an X-ray dosimeter, and a pulse width and pulse count per frame are determined based on that value. For example, let P is a transmittance at which X-rays are transmitted through an element that attenuates an X-ray dose on the sensor front surface. An irradiation time Tx required to set the dose on the sensor to be 3 mR is given by:

$$Tx=3\ mR/(Ax/(T0 \times P))$$

Note that the element that causes the transmittance P is an anti-scattering grid, which normally has a transmittance of 50 to 60%.

Using Tx obtained in this way, the exposure conditions upon dynamic image radiography can be set in the sequence explained in the first embodiment.

Figure 10:
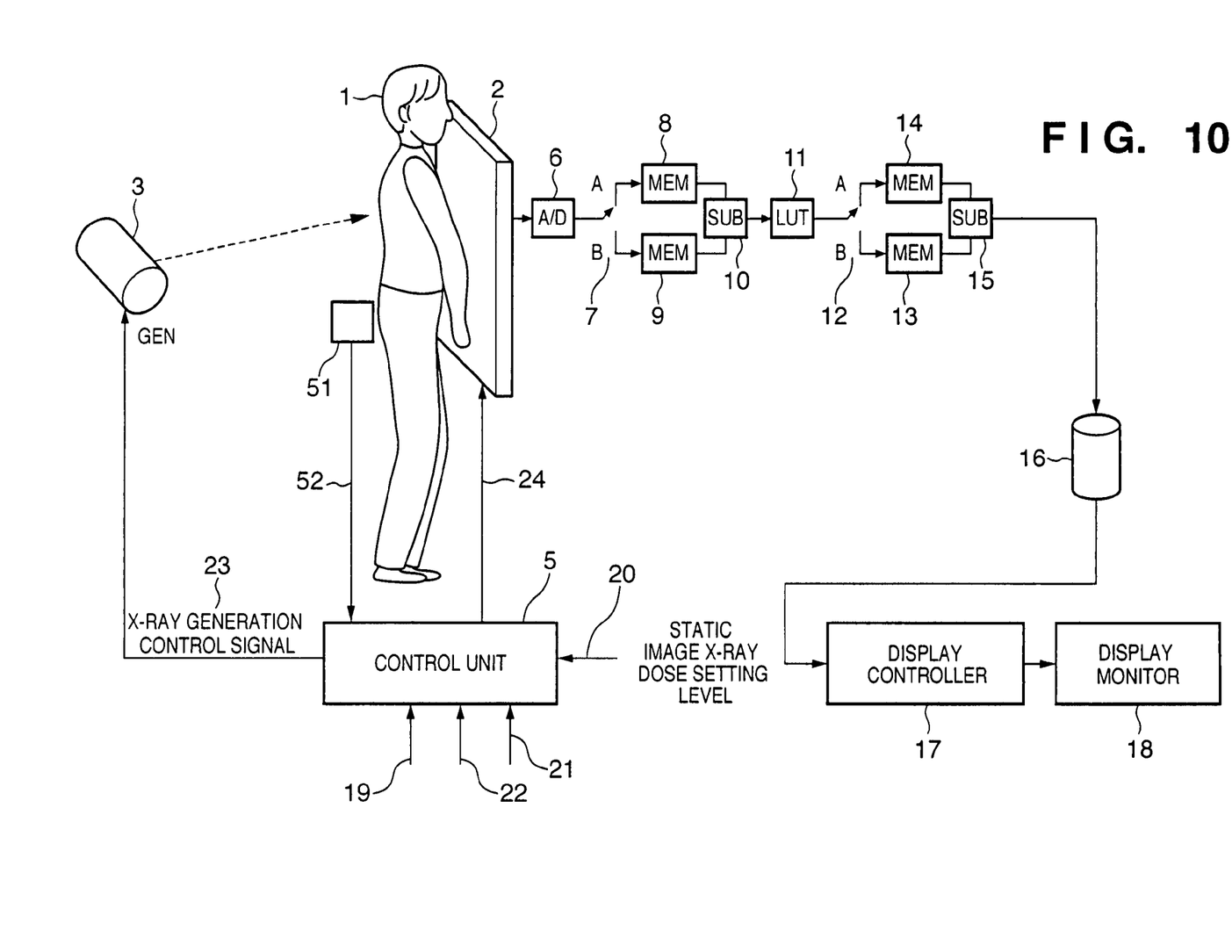
FIG. 10 is a block diagram showing an example of the arrangement of a radiographic image capturing apparatus according to the second embodiment.

In order to adjust the irradiation dose more reliably, as shown in FIG. 10, an X-ray monitor 51 may be provided to a portion which is not related to the subject 1 (the back surface portion of the subject 1 or a direct ray region behind the FPD 2), and may measure the radiation dose during dynamic image radiography. When the output from the X-ray monitor 51 has reached the same dose as that of a static image (a dose equivalent to 3 mR on the sensor front surface), dynamic state observation is ended, thus preventing excessive exposure. For example, when the X-ray monitor 51 is arranged on the back surface portion of the subject 1, dynamic image radiography ends when the integrated value of an X-ray dose becomes 3 mR/P.

Third Embodiment

The third embodiment will explain an arrangement for suitably displaying a dynamic image radiographed like in the first or second embodiment. That is, the control for displaying dynamic image data stored in the data recording device 16 shown in FIG. 1 on the monitor 18 by the display controller 17 will be described in detail below.

Even when the total dose is set to be the same as that of static image radiography in dynamic image radiography, if the dose per frame is too small, a quantization (A/D conversion) error becomes dominant, and a portion which is not imaged or a portion which becomes insignificant even if it is imaged is formed. For example, a mediastimum or abdomen upon chest radiography corresponds to such portion. Hence, in the third embodiment, gray-level transformation is made by ignoring such portion which cannot be radiographed, and only an observable portion is imaged. Upon displaying a dynamic image, it suffices in many cases.

The gray-level transformation process for image display on the monitor 18 is executed by the display controller 17. Normally, the gray-level transformation process uses a lookup table which associates input gray-level values (X-ray doses) and output gray-level values in one-to-one correspondence. In the third embodiment, the lookup table is generated not to image a region with a small dose in accordance with a dynamic image to be displayed, thus attaining gray-level transformation. That is, in the third embodiment, the display controller 17 generates a X-ray dose histogram shown in FIG. 6A for one frame to be displayed, and generates a lookup table shown in FIG. 6B on the basis of this histogram. Then, the display controller 17 stores the generated lookup table in a memory (not shown).

Figure 6A:
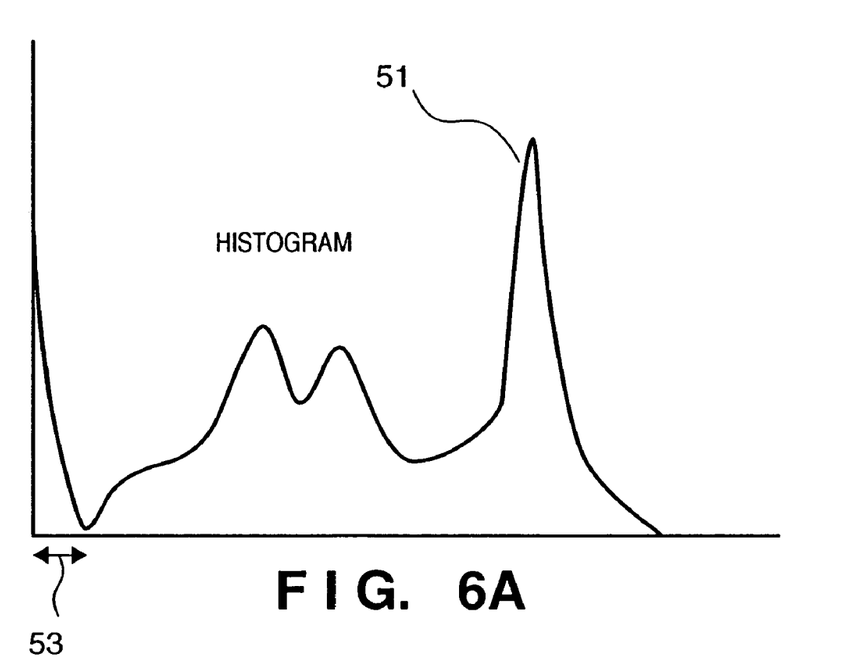
FIGS. 6A and 6B respectively show an example of a histogram upon dynamic image radiography and an example of a lookup table used upon displaying a dynamic image in the third embodiment.
Figure 6B:
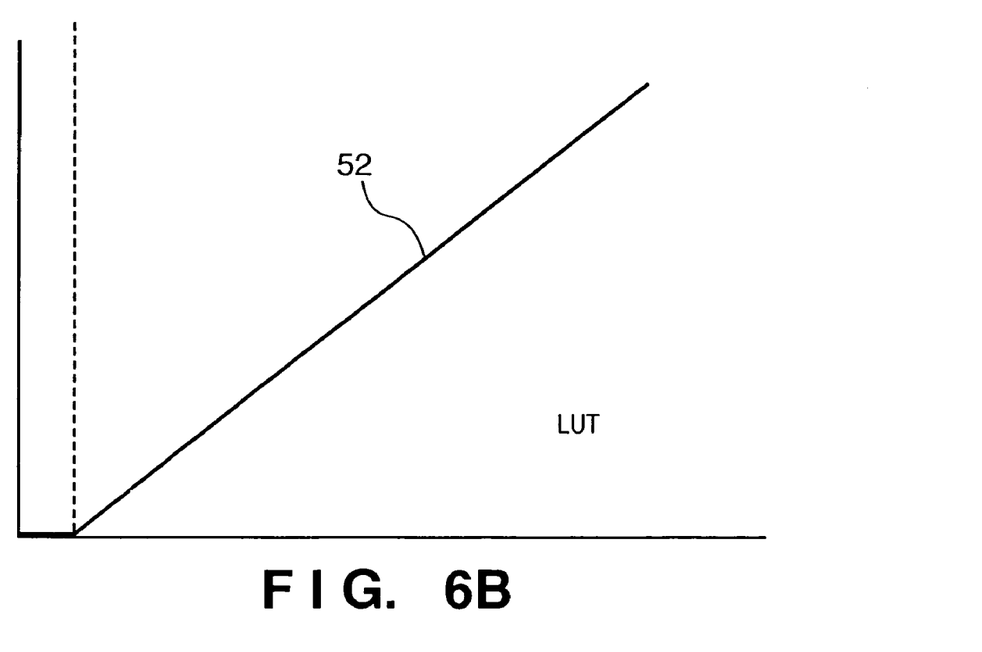

FIG. 6A shows a typical histogram of one frame image in the captured dynamic image; the abscissa plots the pixel value (brightness value), and the ordinate plots the frequency of occurrence. In FIG. 6A, a region 53 has very small data, is buried in quantization noise of A/D conversion, and becomes insignificant if it is imaged intact. Hence, a lookup table (LUT) shown in FIG. 6B is generated to have a setting which does not display the region 53 that cannot be imaged. The display controller 17 sequentially displays images that have undergone gray-level transformation using such lookup table. As a method of setting such region 53, a region of pixel values equal to or lower than a predetermined value may be selected. Alternatively, the region 53 may be determined by generating and analyzing the histogram. In this case, a method of selecting a region of a minimum pixel value or less of the minimal value of the histogram as the region 53 may be used. The analysis of the histogram suffices to be applied to image data of the first frame in the dynamic image. Of course, the analysis of the histogram may be applied to image data of respective frames if the processing performance is allowed.

As described above, according to the display control of the third embodiment, upon displaying a dynamic image in which the total exposure dose of dynamic image radiography is suppressed to be equal to or lower than that of static image radiography, since a dynamic image is reproduced by effectively utilizing dose information which is large enough to be imaged, an unwanted image portion is not reproduced, and a highly recognizable image can be obtained.

Fourth Embodiment

The fourth embodiment increases the display speed upon observing dynamic images captured in the first or second embodiment. With this display, averaging due to the afterimage effect can be promoted, thus improving the recognition ratio. Furthermore, by repetitively displaying a series of dynamic images, the averaging effect and recognition ratio can be improved.

In order to observe a dynamic image captured at a low dose, the afterimage effect of the human eye and recognition can be utilized. Hence, the display speed of a dynamic image is desirably specified upon display. The fourth embodiment implements such display.

Figure 7A:
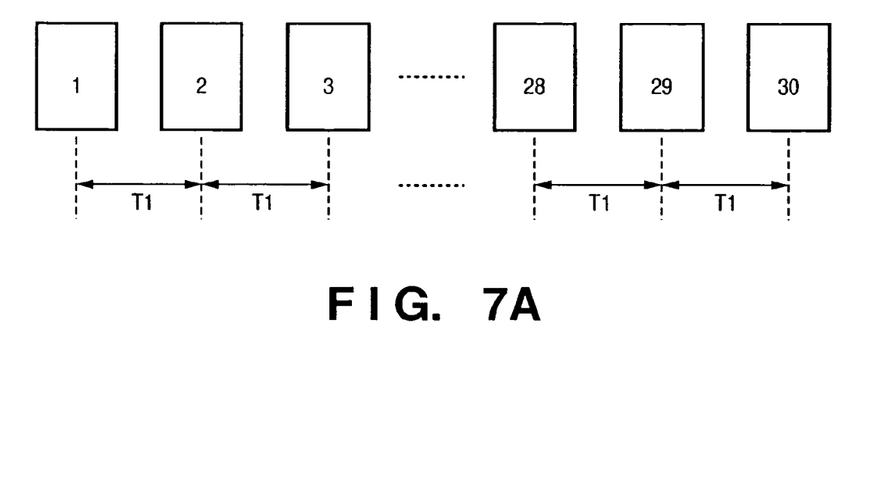
FIGS. 7A and 7B are views for explaining the time intervals of frames upon radiography and display in the fourth embodiment.
Figure 7B:
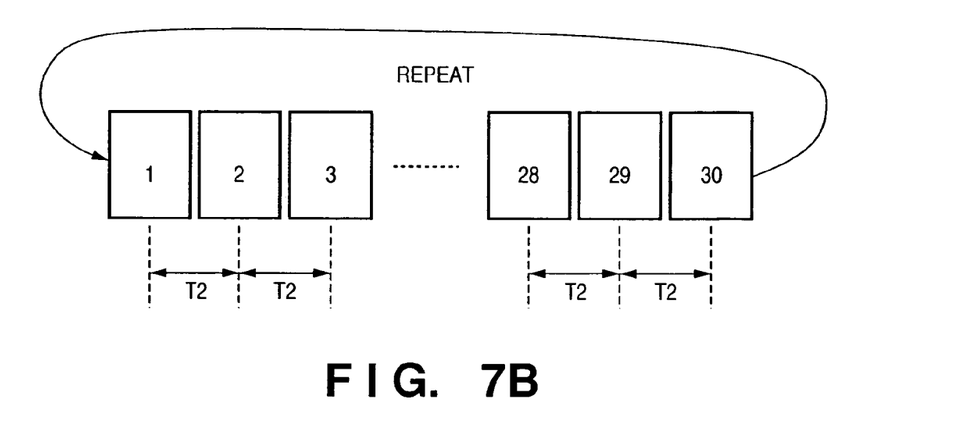

FIG. 7A shows an example of 30 frames of a dynamic image which are captured at time intervals T1, and FIG. 7B shows a state wherein the display interval upon displaying the dynamic image shown in FIG. 7A is set to be T2. In general, by setting T2<T1, the afterimage effect can be improved. As shown in FIG. 7B, by repetitively displaying all the frames (30 frames in the example of FIGS. 7A and 7B) of the dynamic image upon observation, the afterimage effect can be further improved, and a specific part can be traced.

Note that the present inventors found that T2<⅙ sec so as to obtain a stable afterimage effect. Therefore, irrespective of the time intervals assumed as T1, T2 may be set as a constant value equal to or smaller than ⅙ sec. If T2 assumes a constant value irrespective of the frame intervals upon capturing, the observer can stably observe images irrespective of the frame intervals upon capturing.

Fifth Embodiment

In the fifth embodiment, when dynamic images are repetitively displayed as described in the fourth embodiment, upon completion of display of all dynamic images, the dynamic images are then displayed in the reverse order to provide continuity to repetitive dynamic image display, thus improving the image recognition ratio due to afterimage and object tracing.

Figure 8:
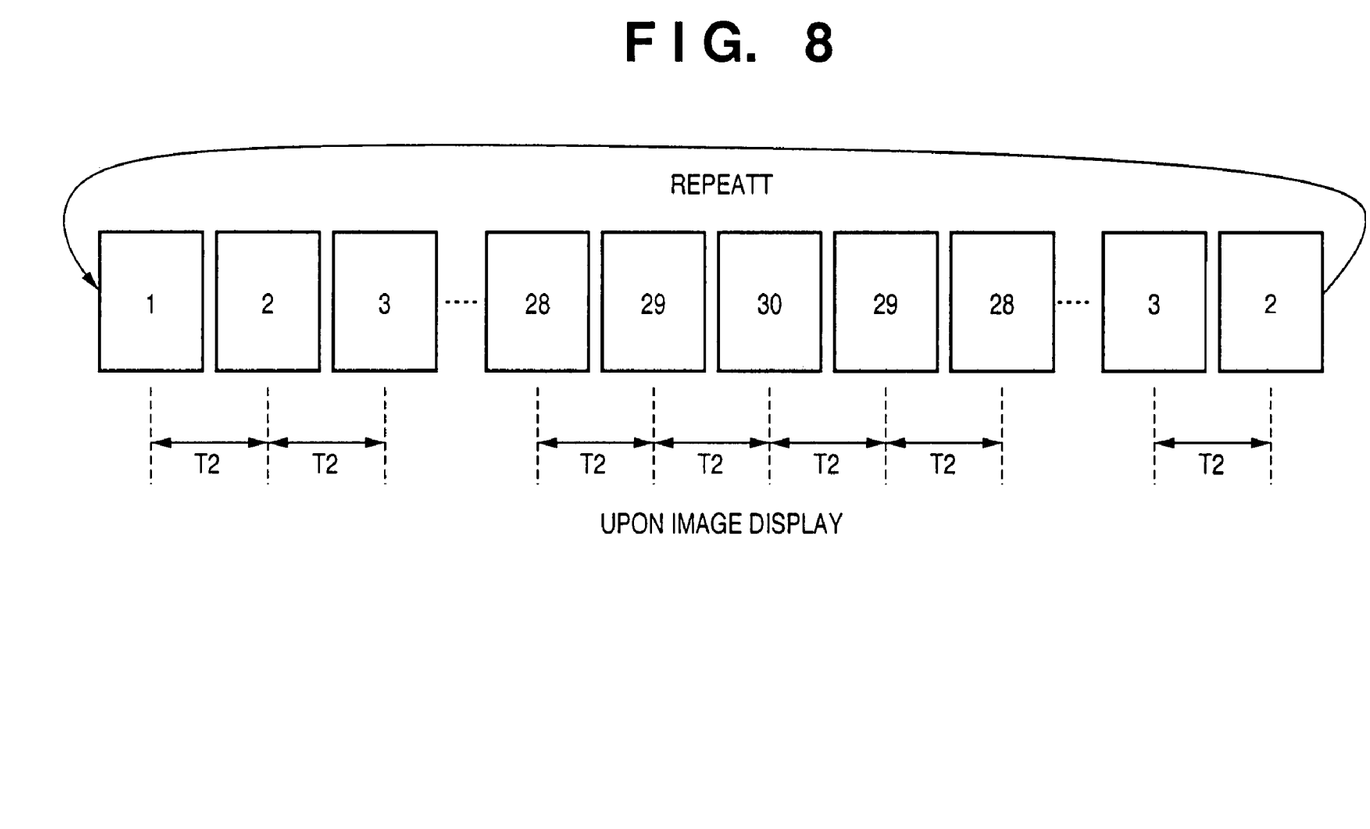
FIG. 8 is a view for explaining the order of repetition of frames in the fifth embodiment.

FIG. 8 is a view for explaining dynamic image display according to the fifth embodiment. In the repetitive display method shown in FIG. 7B, upon completion of display of all frames, display restarts from the first frame. However, in the fifth embodiment, after the first to 30th frames are displayed in turn, the 29th frame, 28th frame, . . . are displayed in descending order. After the first frame is reached, the frames are displayed in ascending order again. With this display method, continuity can be provided to the images. More specifically, according to the display method of the fifth embodiment, images can be repetitively displayed without any disconnection, and the observer can stably trace a part and structure in images, thus allowing stable image observation due to the afterimage effect.

Sixth Embodiment

Furthermore, in the sixth embodiment, upon observing dynamic images captured in the first or second embodiment, images are displayed in a reduced scale compared to an entity, and the dynamic state recognition ratio can be improved due to the reduced-scale display effect (the effect of lowering the noise level per pixel).

Since images captured at a low X-ray dose have a small number of X-ray particles per pixel, they have large variations compared to an average value, and are so-called poor S/N images. Upon observing such images, images may be displayed in a reduced scale so as to improve the S/N within the observable range of the human eye. If a minimum range noticed by the human eye is a [mm], and pixel information is displayed with large variations in that unit, the observer feels variations in pixel information, thus disturbing normal observation. In the normal observation distance, a is about 0.5 mm.

Hence, in the sixth embodiment, upon displaying a dynamic image, reduced-scale display is made by combining surrounding pixels (averaged) to form a new pixel. With such reduced-scale display, variations per pixel can be reduced, and the entire image can be easily observed.

For example, when an image captured by the FPD at 0.2 mm is displayed with that size, the human eye can see variations per pixel. However, when that image is displayed to have an average value of four pixels (2 vertical pixels×2 horizontal pixels) as one pixel, variations per pixel (standard deviation) can be reduced to ½ although the image size becomes ¼, and the observer can observe an image from which noise is reduced.

Figure 9A:
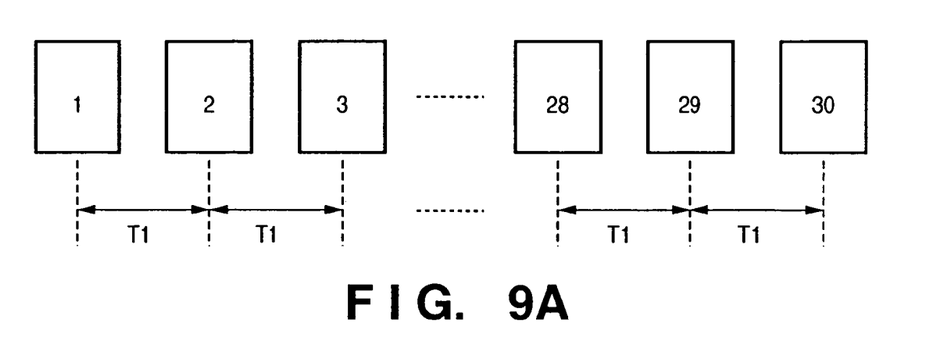
FIGS. 9A and 9B are views for displaying reduced-scale display of frames in the sixth embodiment.
Figure 9B:
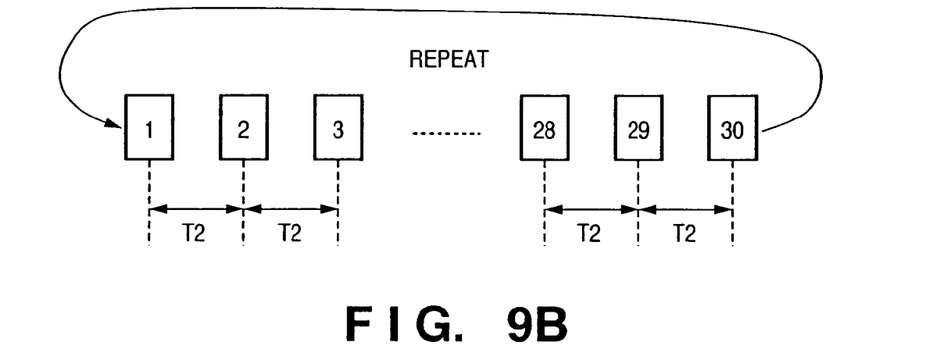

FIG. 9A shows an example of 30 frames of a dynamic image which are captured at the time intervals T1. FIG. 9 shows a case wherein the display interval upon displaying these frames is set to be T2. As has been explained in the fourth and fifth embodiments, T2<T1 is set and display is repeated, thus improving the afterimage effect. Then, when the image size to be displayed is reduced, i.e., images are displayed in a reduced scale, the observability of the entire image is improved. In FIG. 9B, display is repeated in turn from the first frame, as shown in FIG. 7B. Alternatively, frames may be repetitively displayed by return, as shown in FIG. 8. Note that the display methods described in the third to sixth embodiments may be practiced solely or in appropriate combinations.

As described above, according to the above embodiments, when the dynamic state is captured and is observed using an FPD with a relatively low sensitivity, stable dynamic image radiography can be made by setting the total irradiation dose upon dynamic image radiography to be equal to or lower than that for a static image. Furthermore, the gray-level characteristics that ignore a part that cannot be imaged upon display are provided and are combined with display at a higher speed than capturing, repetitive display, repetitive display by return, reduced-scale display, and the like, thus allowing stable observation.

Therefore, according to each of the above embodiments or their combinations, even when, for example, a low-cost FPD is used, dynamic image radiography can be made while preventing an increase in irradiation dose.

As many apparently widely different embodiments of the present invention can be made without departing from the spirit and scope thereof, it is to be understood that the invention is not limited to the specific embodiments thereof except as defined in the appended claims.

CLAIM OF PRIORITY

This application claims priority from Japanese Patent Application No. 2004-136017 filed on Apr. 30, 2004, which is hereby incorporated by reference herein.

What is claimed is:

1. A radiographic image capturing apparatus for capturing radiographic images by controlling a radiation generator and a detection device for converting an intensity distribution of radiation generated by the radiation generator into image information, comprising:

a determination unit configured to determine an exposure condition of each frame in dynamic image radiography so as to set a total irradiation dose of radiation for the dynamic image radiography to be equal to or less than an irradiation dose required for a single static image radiography on the basis of the exposure condition of the dynamic image radiography; and a capturing unit configured to capture a radiographic image of each frame under the exposure condition determined by said determination unit.

2. The apparatus according to claim 1, wherein the exposure condition of the dynamic image radiography includes a total exposure time and frame count of the dynamic image radiography.

3. The apparatus according to claim 1, wherein said determination unit comprises:

a measurement unit configured to measure a radiation irradiation time required for radiation static image radiography using the radiation generator; and a setting unit configured to set a radiation irradiation time and irradiation time interval required to radiograph each frame on the basis of the radiation irradiation time measured by said measurement unit, and the exposure condition.

4. The apparatus according to claim 1, wherein said determination unit comprises:

a calculation unit configured to calculate a radiation irradiation time required for static image radiography on the basis of a radiation dose per unit time generated by the radiation generator; and a setting unit configured to set a radiation irradiation time and irradiation time interval required to capture each frame on the basis of the radiation irradiation time calculated by said calculation unit, and the exposure condition.

5. The apparatus according to claim 4, further comprising:
a unit configured to measure a radiation dose generated by the radiation generator during execution of the dynamic image radiography, and ending the dynamic image radiography when the radiation dose that reaches the detection device reaches a radiation dose required for the single static image radiography.

6. The apparatus according to claim 1, wherein the dynamic image radiography captures at least three frames of an image per sec.

7. The apparatus according to claim 1, wherein said setting unit sets an exposure interval of respective frames on the basis of the total image exposure time of the dynamic image radiography.

8. The apparatus according to claim 7, wherein the total exposure time of the dynamic image radiography is equal to or greater than 5 sec.

9. The apparatus according to claim 1 further comprising:
a detection unit configured to detect a pixel value of a non-imaging area caused by an insufficient radiation dose on the basis of a frequency distribution of pixel values obtained for one of a plurality of frames of radiographic images captured by said capturing unit;

a gray-level transformation unit configured to perform gray-level transformation to ignore pixel values of the non-imaging area detected by said detection unit; and a display unit configured to display image data that has undergone the gray-level transformation by said gray-level transformation unit on a display.

10. The apparatus according to claim 9, wherein said display unit displays images of respective frames at an interval shorter than a time interval between frames upon capturing dynamic images when the dynamic images are displayed.

11. The apparatus according to claim 10, wherein said display unit repetitively displays the dynamic images.

12. The apparatus according to claim 11, wherein said display unit repeats temporally forward display and reserve display upon repetitively displaying the dynamic images.

13. The apparatus according to claim 11, wherein said display unit displays an image reduced to be smaller than a captured image size upon displaying the dynamic images.

14. A radiographic image capturing method for capturing radiographic images by controlling a radiation generator and a detection device for converting an intensity distribution of radiation generated by the radiation generator into image information, comprising:

a determination step of determining an exposure condition of each frame in dynamic image radiography so as to set a total irradiation dose of radiation for the dynamic image radiography to be equal to or less than an irradiation dose required for a single static image radiography on the basis of the exposure condition of the dynamic image radiography; and a capturing step of capturing a radiographic image of each frame under the exposure condition determined in the determination step.

15. A computer-readable medium storing a control program for making a computer execute a radiographic image capturing method of claim 14.

16. The method according to claim 14 further comprising:

a detection step of detecting a pixel value of a non-imaging area caused by an insufficient radiation dose on the basis of a frequency distribution of pixel values obtained for one of the plurality of frames of radiographic images captured in the capturing step;

a gray-level transformation step of performing gray-level transformation to ignore pixel values of the non-imaging area detected in the detection step; and a display step of displaying image data that has undergone the gray-level transformation in the gray-level transformation step on a display.

* * * * *

UNITED STATES PATENT AND TRADEMARK OFFICE
CERTIFICATE OF CORRECTION

PATENT NO.        : 7,221,735 B2  
APPLICATION NO.   : 11/114057  
DATED             : May 22, 2007  
INVENTOR(S)       : Hitoshi Inoue Page 1 of 1

It is certified that error appears in the above-identified patent and that said Letters Patent is hereby corrected as shown below:

SHEET 8

FIG. 8, "REPEATT" should read --REPEAT--.

COLUMN 4

Line 21, "upon" should be deleted.

COLUMN 9

Line 41, "let P" should read --P--.

COLUMN 10

Line 14, "mediastimum" should read --mediastinum--.
Line 29, "a X-ray" should read --an X-ray--; and Signed and Sealed this Twenty Second Day of April, 2008

JON W. DUDAS
*Director of the United States Patent and Trademark Office*